US009242227B2

(12) United States Patent
Dakka et al.

(10) Patent No.: US 9,242,227 B2
(45) Date of Patent: Jan. 26, 2016

(54) DEHYDROGENATION CATALYST AND PROCESS

(75) Inventors: Jihad M. Dakka, Whitehouse Station, NJ (US); Lorenzo C. Decaul, Langhorne, PA (US); Terry E. Helton, Bethlehem, PA (US); Teng Xu, Houston, TX (US); Jenna L. Wallace, Bethlehem, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 154 days.

(21) Appl. No.: 13/515,142

(22) PCT Filed: Dec. 17, 2010

(86) PCT No.: PCT/US2010/061003
§ 371 (c)(1),
(2), (4) Date: Aug. 15, 2012

(87) PCT Pub. No.: WO2011/096990
PCT Pub. Date: Aug. 11, 2011

(65) Prior Publication Data
US 2012/0302799 A1    Nov. 29, 2012

Related U.S. Application Data

(60) Provisional application No. 61/301,799, filed on Feb. 5, 2010.

(30) Foreign Application Priority Data

Mar. 23, 2010    (EP) ..................................... 10157371

(51) Int. Cl.
| | | |
|---|---|---|
| C07C 37/08 | (2006.01) | |
| B01J 23/58 | (2006.01) | |
| B01J 21/08 | (2006.01) | |
| B01J 37/02 | (2006.01) | |
| B01J 37/12 | (2006.01) | |
| C07C 2/74 | (2006.01) | |
| C07C 37/06 | (2006.01) | |
| C07C 45/53 | (2006.01) | |
| C07C 407/00 | (2006.01) | |

(52) U.S. Cl.
CPC B01J 23/58 (2013.01); B01J 21/08 (2013.01); B01J 37/0205 (2013.01); B01J 37/12 (2013.01); C07C 2/74 (2013.01); C07C 37/06 (2013.01); C07C 37/08 (2013.01); C07C 45/53 (2013.01); C07C 407/00 (2013.01); *C07C 2101/14* (2013.01); *C07C 2529/70* (2013.01)

(58) Field of Classification Search
USPC ................. 568/300, 772, 799, 806
See application file for complete search history.

(56) References Cited

U.S. PATENT DOCUMENTS

| | | | |
|---|---|---|---|
| 2,291,585 A | | 7/1942 | Bartlett et al. |
| 3,076,810 A | | 2/1963 | Duggan et al. |
| 3,194,843 A | | 7/1965 | Silber et al. |
| 3,211,668 A | | 10/1965 | Yamamoto |
| 3,238,120 A | | 3/1966 | Sale |
| 3,247,278 A | | 4/1966 | Garwood et al. |
| 3,358,044 A | | 12/1967 | Russell et al. |
| 3,442,958 A | | 5/1969 | Choo |
| 3,514,492 A | | 5/1970 | Juguin et al. |
| 3,519,575 A | | 7/1970 | Bozik et al. |
| 3,534,110 A | * | 10/1970 | Le Page et al. ............... 568/799 |
| 3,534,116 A | | 10/1970 | Fuller et al. |
| 3,580,970 A | | 5/1971 | Swift |
| 3,691,102 A | | 9/1972 | Swift |
| 3,843,560 A | | 10/1974 | Hayes |
| 4,070,413 A | | 1/1978 | Imai |
| 4,088,603 A | | 5/1978 | Carter et al. |
| 4,139,570 A | * | 2/1979 | Antos ........................... 585/434 |
| 4,162,267 A | | 7/1979 | Fisher et al. |
| 4,167,456 A | | 9/1979 | Murtha |
| 4,169,857 A | | 10/1979 | Murtha |
| 4,258,268 A | | 3/1981 | Bjornson |
| 4,328,372 A | | 5/1982 | Wu |
| 4,417,076 A | | 11/1983 | Rozovsky et al. |
| 4,418,237 A | | 11/1983 | Imai |
| 4,434,299 A | | 2/1984 | Chang et al. |
| 4,520,129 A | | 5/1985 | Murtha |
| 4,788,371 A | | 11/1988 | Imai et al. |
| 4,929,762 A | | 5/1990 | Matsunaga et al. |

(Continued)

FOREIGN PATENT DOCUMENTS

| | | |
|---|---|---|
| DE | 100 18 724 | 10/2001 |
| EP | 0 328 507 | 8/1989 |

(Continued)

OTHER PUBLICATIONS

Arends; Tetrahedron, 2002, 58, 9055-9061.*
Saito, Y., et al."Performance of activity test on supported Pd catalysts for dehydrogenation of cyclohexanone to phenol(effect of supports on activity)", Ibaraki Kogyo Koto Senmon Gakko Kenkyu Iho (1995), vol. 30, pp. 39-46—English Abstract Only.
Swift, H. et al., "Metallic Phases and Activites of Nickel—Tin—Silica Catalysts Dehydrogenation of Cyclohexanone, Cyclohexanol, and Cyclohexane", Journal of Catalysis, 1968, vol. 12, pp. 5-14.

(Continued)

Primary Examiner — Sudhakar Katakam
Assistant Examiner — Pancham Bakshi
(74) Attorney, Agent, or Firm — Siwen Chen; Stephen A. Baehl

(57) ABSTRACT

A catalyst composition comprises (i) a support; (ii) a dehydrogenation component comprising at least one metal or compound thereof selected from Groups 6 to 10 of the Periodic Table of Elements; and (iii) potassium or a potassium compound present in an amount of about 0.15 to about 0.6 wt % of potassium based upon the total weight of the catalyst composition, wherein the catalyst composition has an oxygen chemisorption of greater than 50%.

9 Claims, 1 Drawing Sheet

(56) References Cited

U.S. PATENT DOCUMENTS

| | | | |
|---|---|---|---|
| 4,933,507 | A | 6/1990 | Inoki et al. |
| 4,999,326 | A | 3/1991 | Sikkenga et al. |
| 5,057,296 | A | 10/1991 | Beck |
| 5,087,792 | A | 2/1992 | Cottrell et al. |
| 5,102,643 | A | 4/1992 | Kresge et al. |
| 5,180,871 | A | 1/1993 | Matsunaga et al. |
| 5,232,580 | A * | 8/1993 | Le et al. .................. 208/114 |
| 5,256,348 | A | 10/1993 | Waller |
| 3,775,487 | A | 11/1993 | Isbitsky et al. |
| 5,292,960 | A | 3/1994 | Meier et al. |
| 5,310,713 | A | 5/1994 | Kojima et al. |
| 5,319,148 | A | 6/1994 | Karcher et al. |
| 5,395,976 | A | 3/1995 | Scharschmidt et al. |
| 5,569,635 | A | 10/1996 | Moy et al. |
| 5,633,421 | A | 5/1997 | Iezzi et al. |
| 6,037,513 | A | 3/2000 | Chang et al. |
| 6,376,422 | B1 | 4/2002 | McNabb et al. |
| 6,417,135 | B1 | 7/2002 | Dyroff |
| 6,579,821 | B1 | 6/2003 | Ginosar et al. |
| 6,916,756 | B2 | 7/2005 | Schindler et al. |
| 7,115,538 | B2 | 10/2006 | Buchanan et al. |
| 7,256,149 | B2 | 8/2007 | Grey et al. |
| 7,285,512 | B2 | 10/2007 | Bai et al. |
| 7,285,685 | B2 | 10/2007 | Walsdorff et al. |
| 7,396,798 | B2 | 7/2008 | Ma et al. |
| 7,538,066 | B2 | 5/2009 | Soled et al. |
| 7,579,511 | B1 * | 8/2009 | Dakka et al. .................. 585/316 |
| 8,183,424 | B2 | 5/2012 | Levin et al. |
| 8,487,140 | B2 * | 7/2013 | Buchanan et al. ............ 568/799 |
| 2003/0083527 | A1 | 5/2003 | Kuhnle et al. |
| 2004/0110630 | A1 | 6/2004 | Schmidt et al. |
| 2007/0032681 | A1 | 2/2007 | Walsdorff et al. |
| 2008/0039315 | A1 | 2/2008 | Ma et al. |
| 2009/0215612 | A1 | 8/2009 | McCarthy et al. |
| 2010/0075842 | A1 | 3/2010 | Han et al. |
| 2011/0037022 | A1 | 2/2011 | Dakka et al. |
| 2012/0149958 | A1 | 6/2012 | Ellrich et al. |

FOREIGN PATENT DOCUMENTS

| | | |
|---|---|---|
| EP | 1 050 339 | 11/2000 |
| EP | 1 288 188 | 3/2003 |
| FR | 1509921 | 1/1968 |
| FR | 1541720 | 10/1968 |
| GB | 986931 | 3/1965 |
| GB | 1013715 | 12/1965 |
| JP | 06-263668 | 9/1994 |
| JP | 07-188082 | 7/1995 |
| JP | 2637812 | 8/1997 |
| JP | 2007/269522 | 10/2007 |
| WO | 91/06616 | 5/1991 |
| WO | 00/67902 | 11/2000 |
| WO | WO 2007/009904 | 1/2007 |
| WO | WO 2008/128638 | 10/2008 |
| WO | WO 2009/131769 | 10/2009 |
| WO | WO 2009/134514 | 11/2009 |
| WO | 2010/024975 | 3/2010 |

OTHER PUBLICATIONS

Milczanowski, S., et al., "Catalytic Dehydrogenation of Cyclohexanone to Phenol", PrZEMYSL Cheniczny, 1978, vol. 57, No. 3, pp. 129-130—English Abstract Only.

Waligora, B., et al., "Catalytic Dehydrogenation of Mixture of Cyclohexanol and Cyclohexanon to Phenol", Prace Chemiczne, 1982, vol. 27, pp. 93-99—English Abstract Only.

R.B. Borade et al., "Selective dehydrogenation of cyclohexene to benzene using Pd-exchanged α-zirconium phosphate", Catalysis Letters, vol. 45, pp. 233-235, 1997.

A. Corma, "From Microporous to Mesoporous Molecular Sieve Materials and Their Use in Catalysis", Chem. Rev., vol. 97, pp. 2373-2419, 1997.

S. Kamiguchi et al., "Catalytic Hydrodehydration of Cyclohexanone, Hydrogenation of 2-Cyclohexen-1-one, and Dehydrogenation of Cyclohexene over a Mo Chloride Cluster with an Octahedral Metal Framework", Journal of Cluster Science, vol. 16, No. 1, pp. 77-91, 2005.

M. Lezanska et al., "Characterization of Cr-MCM-41 and Al, Cr-MCM-14 Mesoporous Catalyst for Gas-Phase Oxidative Dehydrogenation of Cyclohexane", J. Phys.Chem. C., vol. 111, pp. 1830-1839, 2007.

M. Masai et al., "Dehydrogenation Activity of Nickel—Tin—Silica Catalyst", Journal of Catalysis, vol. 38, pp. 128-134, 1975.

M.C. Samolada et al., "Catalyst Evaluation for Catalytic Biomass Pyrolysis", Energy & Fuels, vol. 14, pp. 1161-1167, 2000.

B. Solsona et al., "Vanadium Oxide Supported on Mesoporous MCM-41 as Selective Catalyst in the Oxidative Dehydrogenation of Alkanes", Journal of Catalysis, vol. 203, pp. 443-452, 2001.

W. Spieker et al., "Experimental Investigation and Modeling of Platinum Adsorption onto Ion-modified Silica and Alumina", Studies in Surface Science and Catalysis, vol. 130, pp. 203-208, 2000.

Fridman et al., "Dehydrogenation of Cyclohexanol on Copper-Containing Ctalysts:I. The Influence of the Oxidation State of Copper on the Activity of Copper Sites", Journal of Catalysis, vol. 195, No. 1, pp. 20-30, 2000.

Cesar et al., "Stability and Selectivity of Bimetallic Cu—Co/SiO2 Catalysts for Cyclohexanol Dehydrogenation", Applied Catalysis A: General, vol. 176, No. 2, pp. 205-212, 1999.

Chen et al., "Nonoxidative Dehydrogenation of Cyclohexanol over Copper—Iron Binary Oxides", Applied Catalysis A: General, vol. 83, No. 2, pp. 201-211, 1992.

Dobrovolszky et al., "Catalytic Transformation of Cyclohexanol on Group VIII Metal Catalysts", Journal of Catalysis, 1982, vol. 74, No. 1, pp. 31-34.

Masai et al., "Dehydrogenation and Hydrogenation Activity of Palladium—Tin—Silica and Nickel—Tin—Silica", Journal of Catalysis, 1977, vol. 50, No. 3, pp. 419-428.

Paal et al., "A Radiotracer Investigation of Transformations of Cyclohexanol in the Presence of a Nickel Powder Catalyst", Z Phys Chem, 1974, vol. 91, No. 1-4, pp. 54-66.

Nikiforova et al., "Dehydrogenation of Cyclohexanol over Copper Supported on Magnesia", Neftekhimiya, 1972, vol. 12, No. 4, pp. 475-480.

Fridman et al., "Dehydrogenation of Cyclohexanol Over Copper—Zinc Catalysts", Neftekhimiya 1989, vol. 29, No. 1, pp. 48-51. (Abstract Only).

* cited by examiner

DEHYDROGENATION CATALYST AND PROCESS

PRIORITY CLAIM

This application is a National Stage Application of International Application No. PCT/US2010/061003 filed Dec. 17, 2010, which claims priority to U.S. Application Ser. No. 61/301,799, filed Feb. 5, 2010, and EP Application Serial No. 10157371.5, filed Mar. 23, 2010, both of which are incorporated herein by reference in their entirety.

CROSS REFERENCE TO RELATED APPLICATIONS

This application is related to U.S. Publication No. WO2009/134514, published Nov. 5, 2009; U.S. Publication No. WO2010/024975, published Mar. 4, 2010; U.S. Application Ser. No. 61/301,780, filed Feb. 5, 2010; U.S. Application No. 61/301,786, filed Feb. 5, 2010; U.S. Application No. 61/301,794, filed Feb. 5, 2010; U.S. Application No. 61/301,799, filed Feb. 5, 2010; U.S. Application No. 61/391,832, filed Oct. 11, 2010; U.S. Application No. 61/424,242, filed Dec. 17, 2010; and International Application No. WO2011/096989, published Aug. 11, 2011.

FIELD

The present invention relates to a dehydrogenation catalyst, its synthesis and its use in the dehydrogenation of cyclohexanone to produce phenol.

BACKGROUND

Currently, the most common route to produce phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone.

Another process involves the hydroalkylation of benzene to produce cyclohexylbenzene, followed by the oxidation of the cyclohexylbenzene to cyclohexylbenzene hydroperoxide, which is then cleaved to produce phenol and cyclohexanone in substantially equimolar amounts. Such a process is described in, for example, U.S. Pat. No. 6,037,513.

In some embodiments, cyclohexanone is converted via dehydrogenation to additional phenol (see International Patent Publication No. WO2010/024975). Such a dehydrogenation step is generally achieved by contacting the cyclohexanone with a supported noble metal catalyst at a temperature of about 250° C. to about 500° C.

For example, U.S. Pat. No. 3,534,110 discloses a process for the catalytic dehydrogenation of cyclohexanone and/or cyclohexanol to phenol over a catalyst comprising platinum and preferably iridium on a silica support. The catalyst also contains 0.5 to 3 wt % of an alkali or alkaline earth metal compound, which, according to column 3, lines 43 to 49, should be incorporated after addition of the platinum since otherwise the resulting catalyst composition has inferior activity, selectivity, and life.

In addition, U.S. Pat. No. 3,580,970 discloses a process for the dehydrogenation of cycloaliphatic alcohols and ketones to the corresponding hydroxyaromatic alcohols in the presence of a catalyst comprising a Group VIII metal, particularly nickel, and tin in a molar amount of about 1.7 to about 15 moles of Group VIII metal per mole of tin. The catalyst may further comprise an alkali metal stabilizing agent in an amount between about 0.3 to about 10 parts by weight of an alkali metal sulfate per part by weight of the Group VIII metal.

U.S. Pat. No. 4,933,507 discloses a method of dehydrogenating cyclohexenone to phenol comprising reacting hydrogen and cyclohexenone in the vapor phase in a molar ratio of 0.5 to 4.0 moles of hydrogen per mole of cyclohexenone at a pressure of at least one atmosphere and a reaction temperature of 300° C. to 500° C. using a solid phase catalyst containing platinum, in the range of 0.2 to 10 wt % of the sum of the catalyst plus support, and an alkali metal, in the range of 0.2 to 3.0 calculated in terms of the weight ratio of $K_2CO_3$ to platinum, both the platinum and the alkali metal being carried on a support.

U.S. Pat. No. 7,285,685 discloses a process for the dehydrogenation of a saturated carbonyl compound, such as cyclohexanone, in the gas phase over a heterogeneous dehydrogenation catalyst comprising platinum and/or palladium and tin on an oxidic support, such as zirconium dioxide and/or silicon dioxide. In general, the dehydrogenation catalyst contains from 0.01 to 2 wt %, preferably from 0.1 to 1 wt %, particularly preferably from 0.2 to 0.6 wt %, of palladium and/or platinum and from 0.01 to 10 wt %, preferably from 0.2 to 2 wt %, particularly preferably from 0.4 to 1 wt %, of tin, based on the total weight of the dehydrogenation catalyst. In addition, the dehydrogenation catalyst can further comprise one or more elements of Groups I and/or II, preferably potassium and/or cesium, in an amount of from 0 to 20 wt %, preferably from 0.1 to 10 wt %, particularly preferably from 0.2 to 1.0 wt %, based on the total weight of the catalyst.

Research into metal-containing cyclohexanone dehydrogenation catalysts has now shown that, although potassium plays a positive role in improving the stability of the dehydrogenation metal, depending on the amount of potassium present, potassium can also have an adverse effect on the phenol selectivity of the catalyst by increasing the formation of unwanted by-products. Surprisingly, however, it has been found that by controlling the potassium content within very narrow limits, between 0.15 and 0.6 wt %, it is possible to achieve optimal phenol selectivity while retaining enhanced stability of the dehydrogenation metal.

SUMMARY

Accordingly, the invention resides in one aspect in a catalyst composition comprising (i) a support; (ii) a dehydrogenation component comprising at least one metal or compound thereof selected from Groups 6 to 10 of the Periodic Table of Elements; and (iii) potassium or a potassium compound present in an amount of about 0.15 to about 0.6 wt % of potassium based upon the total weight of the catalyst composition, wherein the catalyst composition has an oxygen chemisorption of greater than 50%.

Conveniently, the potassium is present in an amount of about 0.2 to about 0.5 wt % of potassium based upon the total weight of the catalyst composition.

Conveniently, the support is selected from the group consisting of silica, a silicate, an aluminosilicate, zirconia, carbon, and carbon nanotubes, especially silica.

Conveniently, the dehydrogenation component comprises at least one of platinum, palladium and compounds thereof, especially platinum or a compound thereof.

Conveniently, the dehydrogenation component is present in an amount of about 0.01 to about 2 wt %, such as about 0.5 to about 1.5 wt % of metallic platinum, based upon the total weight of the catalyst composition.

In a further aspect, the invention resides in a method for preparing a catalyst composition, the method comprising:

(a) treating a support with potassium or a compound thereof in an amount to provide about 0.15 to about 0.6 wt % based upon the total weight of the catalyst composition;

(b) calcining the treated support, conveniently in an oxygen-containing atmosphere, at a temperature of about 100° C. to about 700° C.; and (c) impregnating the support with a dehydrogenation component comprising at least one metal or compound thereof selected from Groups 6 to 10 of the Periodic Table of Elements, wherein the impregnating (c) is effected after or at the same time as the treating (a). Generally, the impregnating (c) is affected after the treating (a) and the calcining (b).

Conveniently, the method further comprises:

(d) calcining the impregnated support at a temperature of about 100° C. to about 600° C.

Conveniently the calcining (d) is conducted in an oxygen-containing atmosphere at a temperature of about 200° C. to about 500° C., such as about 300° C. to about 450° C., for a time of about 1 to about 10 hours.

In yet a further aspect, the invention resides in a process for the dehydrogenation of cyclohexanone to produce phenol, the process comprising contacting a feed comprising cyclohexanone under dehydrogenation conditions with catalyst composition comprising (i) a support; (ii) a dehydrogenation component comprising at least one metal or compound thereof selected from Groups 6 to 10 of the Periodic Table of Elements; and (iii) potassium or a potassium compound present in an amount of about 0.15 to about 0.6 wt % of potassium based upon the total weight of the catalyst composition.

In still yet a further aspect, the invention resides in a process for producing phenol from benzene, the process comprising:

(a) reacting benzene and hydrogen with a catalyst under hydroalkylation conditions to produce cyclohexylbenzene;

(b) oxidizing cyclohexylbenzene from (a) to produce cyclohexylbenzene hydroperoxide;

(c) converting cyclohexylbenzene hydroperoxide from (b) to produce an effluent steam comprising phenol and cyclohexanone; and (d) contacting at least a portion of the effluent stream from (c) with a dehydrogenation catalyst comprising: (i) a support; (ii) a dehydrogenation component comprising at least one metal or compound thereof selected from Groups 6 to 10 of the Periodic Table of Elements; and (iii) potassium or a potassium compound present in an amount of about 0.15 to about 0.6 wt % of potassium based upon the total weight of the catalyst composition, wherein the contacting occurs under dehydrogenation conditions effective to convert at least part of the cyclohexanone in the effluent stream into phenol and hydrogen.

Conveniently, said dehydrogenation conditions comprise a temperature of about 250° C. to about 500° C., a pressure of about 100 to about 3550 kPa, a weight hourly space velocity of about 0.2 to 50 hr$^{-1}$, and a hydrogen to cyclohexanone-containing feed molar ratio of about 2 to about 20.

DETAILED DESCRIPTION OF THE EMBODIMENTS

Figure 1:
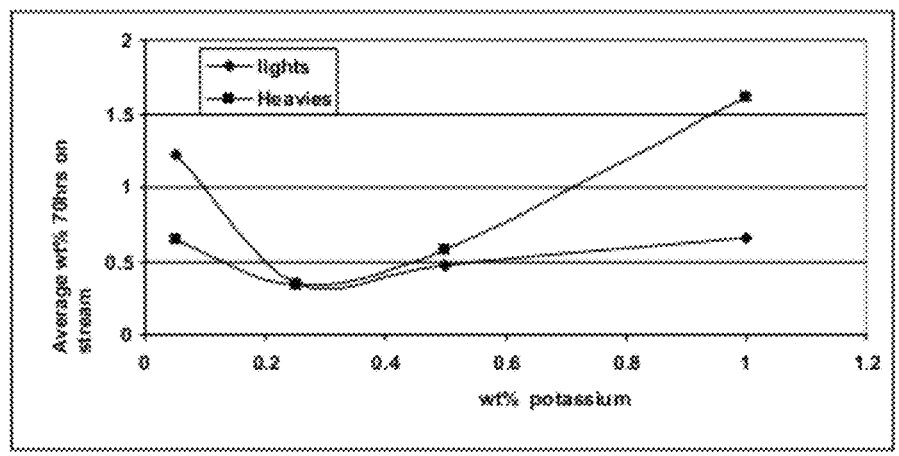
FIG. 1 is a graph of average lights and heavies production after 70 hours on stream against the potassium (K) concentration of the catalyst in the process of dehydrogenating cyclohexanone described in Example 7.

Described herein is a catalyst composition and a method of its synthesis, in which the catalyst composition comprises: (i) a support; (ii) a dehydrogenation component comprising at least one metal or compound thereof selected from Groups 6 to 10 of the Periodic Table of Elements; and (iii) potassium or a potassium compound present in an amount of about 0.15 to about 0.6 wt % of potassium based upon the total weight of the catalyst composition. The catalyst composition is useful in the dehydrogenation of cycloaliphatic alcohols and ketones to the corresponding hydroxyaromatic alcohols and, in particular, in the dehydrogenation of cyclohexanone to produce phenol.

In one preferred embodiment, the present catalyst is employed to dehydrogenate cyclohexanone produced as a by-product in an integrated process for producing phenol via cyclohexylbenzene. In this process, benzene is hydroalkylated to produce cyclohexylbenzene, which then undergoes oxidation and cleavage to produce phenol and cyclohexanone. The cyclohexanone is then dehydrogenated to produce additional phenol together with hydrogen which is desirably recycled to the benzene hydroalkylation step. The present catalyst will therefore now be more particularly with reference to this preferred embodiment, although it will be appreciated that the catalyst can be employed to dehydrogenate other cycloaliphatic alcohols and ketones to their corresponding hydroxyaromatic alcohols.

Production of Cyclohexylbenzene

In the integrated process for producing phenol and cyclohexanone from benzene, the benzene is initially converted to cyclohexybenzene by any conventional technique, including alkylation of benzene with cyclohexene in the presence of an acid catalyst, such as zeolite beta or an MCM-22 family molecular sieve, or by oxidative coupling of benzene to make biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

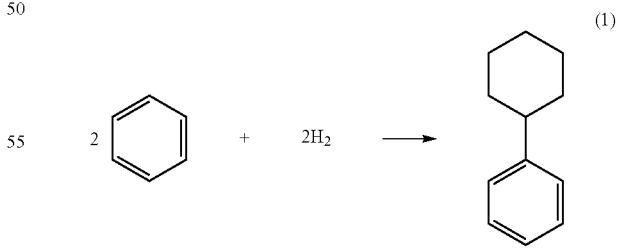

(1)

For an example of hydroalkylation of benzene in the presence of hydrogen for the production of cyclohexylbenzene, see U.S. Pat. Nos. 6,730,625 and 7,579,511 which are incorporated by reference. Also, see International Applications WO2009131769 or WO2009128984 directed to catalytic hydroalkylation of benzene in the presence of hydrogen for the production of cyclohexylbenzene.

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes molecular sieves having the MWW framework topology. (Such crystal structures are discussed in the "Atlas of Zeolite Framework Types", Fifth edition, 2001, the entire content of which is incorporated as reference.)

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Ga. and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction is highly selective towards cyclohexylbenzene, the effluent from the hydroalkylation reaction will normally contain some dialkylated products, as well as unreacted benzene and the desired monoalkylated species. The unreacted benzene is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, zeolite USY, and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

One by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 500 psig (100 to 3550 kPa, gauge), a weight hourly space velocity of about 0.2 to 50 hr$^{-1}$, and a hydrogen to hydrocarbon feed molar ratio of about 0 to about 20.

The cyclohexylbenzene product from the hydroalkylation reaction can be fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent is subjected to a cleavage reaction to convert the cyclohexyl-1-phenyl-1-hydroperoxide to phenol and cyclohexanone. Cleavage may be conducted on oxidation reaction effluent, with or without the effluent undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3 A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939.

Hydroperoxide Cleavage

The final reactive step in the conversion of the cyclohexylbenzene into phenol and cyclohexanone involves the acidcatalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to and to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone, hydroxyhexaphenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Suitable cleavage conditions include a temperature of greater than 50° C. and no greater than 200° C., or at least 55° C. and no greater than 120° C., and a pressure of at least 1 and no greater than 370 psig (at least 7 and no greater than 2,550 kPa, gauge), or at least 14.5 and no greater than 145 psig (at least 100 and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone, each of which generally comprises about 40 to about 60 wt %, or about 45 to about 55 wt % of the cleavage reaction product, such wt % based on the weight of the cleavage reaction product exclusive of unreacted cyclohexylbenzene and acid catalyst.

The cleavage reaction product may contain unreacted acid catalyst and hence at least a portion of the cleavage reaction product may be neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide and barium hydroxide. Sodium and potassium carbonates may also be used, optionally at elevated temperatures. Other suitable known or hereinafter devised basic materials may also be used.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Suitable neutralization conditions may include a pressure of about 1 to about 500 psig (5 kPa to 3450 kPa, gauge), or about 10 to 200 psig (70 to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which is then treated to convert at least part of the cyclohexanone to additional phenol.

Cyclohexanone Dehydrogenation

In order to maximize the production of phenol from the benzene starting material, at least part of the cyclohexanone in the cleavage effluent may be subjected to dehydrogenation according to the following reaction:

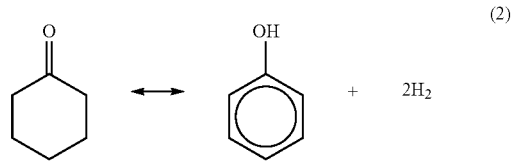

In one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to said dehydrogenation reaction contains less than 50 wt %, for example less than 30 wt %, such as less than 1 wt %, phenol. Separation steps can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

The catalyst employed in the cyclohexanone dehydrogenation reaction comprises (i) a support; (ii) a dehydrogenation component comprising at least one metal or compound thereof selected from Groups 6 to 10 of the Periodic Table of Elements; and (iii) potassium or a potassium compound present in an amount of about 0.15 to about 0.6 wt % of potassium based upon the total weight of the catalyst composition.

The catalyst support is typically formed of silica, a silicate, an aluminosilicate, carbon, or carbon nanotubes. In one embodiment, the support comprises a crystalline, mesoporous silicate material selected from MCM-41, MCM-48 and MCM-50. In other embodiments, the silica support has a surface area as measured by ASTM D3663 in the range from about 10 m$^2$/gram to about 1000 m$^2$/gram, such as from about 20 m$^2$/gram to about 500 m$^2$/gram, a pore volume in the range of from about 0.2 cc/gram to about 3.0 cc/gram and a median pore diameter in the range from about 10 angstroms to about 2000 angstroms, such as from about 20 angstroms to about 500 angstrom. Such pore volume and median pore diameter values are determined by mercury intrusion porosimetry as described in ASTM D4284. The support may or may not comprise a binder. Suitable silica supports are described in, for example, PCT Pub. No. WO/2007084440 A1 filed on Jan. 12, 2007 and entitled "Silica Carriers" and is hereby incorporated by reference for this purpose.

Generally, the dehydrogenation component comprises at least one metal component selected from Groups 6 to 10 of the Periodic Table of Elements, such as platinum and palladium.

Typically, the metal component is present in an amount between about 0.1 wt % and about 10 wt % of the catalyst. In one embodiment, the dehydrogenation component is present in an amount between about 0.1 wt % and about 5 wt % of the catalyst or between about 0.2 wt % and about 4 wt % of the catalyst or between about 0.3 wt % and about 3 wt % of the catalyst or between about 0.4 wt % and 2 wt % of the catalyst.

It will be understood that the potassium in the catalyst composition may not be purely the elemental metal, but could, for example, be at least partly in another form, such as a salt, oxide, chloride, hydride, sulfide, carbonate, etc. For purposes of this application, the wt % of potassium or potassium compound in the catalyst composition is calculated based upon the amount of potassium used to form the catalyst composition. For purposes of illustration, a catalyst composition made with 5.21 grams of potassium carbonate (3.0 grams of potassium) and 66.87 grams of tetraammine platinum hydroxide solution (4.486 wt % Pt) that is supported on 294 grams of silicon dioxide contains 1 wt % of potassium and 1 wt % Pt, based upon total weight of the catalyst composition.

Moreover, for purposes of determining wt %s of various components, only that portion of the support that supports the dehydrogenation component and/or the potassium or potassium compound shall be considered.

The dehydrogenation catalyst is typically prepared by sequentially or simultaneously treating the support, such as by impregnation, with one or more liquid compositions comprising the dehydrogenation component or a precursor thereof and the potassium or potassium compound or a precursor thereof in a liquid carrier, such as water. An organic dispersant may be added to each liquid carrier to assist in uniform application of the metal component(s) to the support. Suitable organic dispersants include amino alcohols and amino acids, such as arginine. Generally, the organic dispersant is present in the liquid composition in an amount between about 1 and about 20 wt % of the liquid composition.

In one preferred embodiment, the catalyst is prepared by sequential impregnation with the potassium being applied to the support before the dehydrogenation component.

After application of one or more of the dehydrogenation metal and the potassium to the support, the support is preferably heated at a temperature of about 100° C. to about 700° C. for example about 200° C. to about 500° C., such as 300° C. to about 450° C., for a time of about 0.5 to about 50 hours, such as about 1 to about 10 hours. In addition to removing any liquid carrier and dispersant used to apply the metal component to the support, the heating is believed to assist in bonding the metal to the support and thereby improve the stability of the final catalyst. The heating is preferably conducted in an oxidizing atmosphere, such as air, although a reducing atmosphere, such as hydrogen, can also be employed.

In one embodiment, the dehydrogenation catalyst has an oxygen chemisorption value of greater than about 30%, such as greater than about 40%, for example greater than about 50%, even greater than about 60%, greater than about 70%, or even greater than about 80%. As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]*100%. The oxygen chemisorption values referred to herein are measured using the following technique. Oxygen chemisorption measurements are obtained using the Micromeritics ASAP 2010. Approximately 0.3 to 0.5 grams of catalyst are placed in the Micrometrics device. Under flowing helium, the catalyst is ramped from ambient (i.e., 18° C.) to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen and hydrogen isotherm is collected in increments at 35° C. between 0.50 and 760 mm Hg. Extrapolation of the linear portion of this curve to zero pressure gives the total (i.e., combined) adsorption uptake.

Suitable conditions for the dehydrogenation step comprise a temperature of about 250° C. to about 750° C., a pressure of about 0.01 atm to about 500 psig (1 to 3450 kPag, gauge), and a weight hourly space velocity (WHSV) of about 2 to 50 hr$^{-1}$, for example a temperature of about 250° C. to about 500° C. and a pressure of about 100 kPa to about 2000 kPa, such as a temperature of about 300° C. to about 450° C. and a pressure of about 100 kPa to 300 kPa. To improve catalyst stability and assist in extracting the hydrogen generated in the dehydrogenation reaction, hydrogen may be cofed to the dehydrogenation reaction, typically such that the molar ratio of hydrogen to cyclohexanone in the dehydrogenation feed is about 0:1 to about 20:1.

The reactor configuration used for the dehydrogenation process generally comprises one or more fixed bed reactors containing the dehydrogenation catalyst. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably the last bed in the series runs at a higher exit temperature than the first bed in the series.

The effluent from the cyclohexanone dehydrogenation reaction is composed mainly of phenol and hydrogen. The desired phenol is easily removed from the reaction effluent by fractionation to leave a hydrogen stream which, after suitable purification, can be recycled to the benzene hydroalkylation step.

By employing the present dehydrogenation process, substantially all the cyclohexanone in the cyclohexylbenzene hydroperoxide cleavage effluent can be converted to phenol. In practice, however, depending on market conditions, there is likely to be a significant demand for cyclohexanone product. This can readily met using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

The invention will now be more particularly described with reference to the following non-limiting Examples and the accompanying drawings.

Example 1

1% Pt, 0.05% K on a Silica Support

A 1/20 inch (0.13 cm) quadrulobe silica extrudate was impregnated with 0.05 wt % K as potassium carbonate using incipient wetness impregnation and dried at 121° C. After drying the 0.05 wt % potassium containing silica extrudate was calcined in air at 538° C. The calcined 0.05% K containing silica extrudate was then impregnated with 1% Pt as tetraammine platinum hydroxide using incipient wetness impregnation and dried at 121° C. After drying the 1% Pt, 0.05% K containing silica extrudate was calcined in air at 350° C. for 3 hrs.

Example 2

1% Pt, 0.25% K on a Silica Support

A 1/20 inch (0.13 cm) quadrulobe silica extrudate was impregnated with 0.25 wt % K as potassium carbonate using incipient wetness impregnation and dried at 121° C. After drying the 0.25 wt % potassium containing silica extrudate was calcined in air at 538° C. The calcined 0.25% K containing silica extrudate was then impregnated with 1% Pt as tetraammine platinum hydroxide using incipient wetness impregnation and dried at 121° C. After drying the 1% Pt, 0.25% K containing silica extrudate was calcined in air at 350° C. for 3 hrs.

Example 3

1% Pt, 0.50% K on a Silica Support

A 1/20 inch (0.13 cm) silica extrudate was impregnated with 0.50 wt % K as potassium carbonate using incipient wetness impregnation and dried at 121° C. After drying the 0.50 wt % potassium containing silica extrudate was calcined in air at 538° C. for 3 hrs. The calcined 0.50% K containing silica extrudate was then impregnated with 1% Pt as tetraammine platinum hydroxide using incipient wetness impregnation and dried at 121° C. After drying the 1% Pt, 0.50% K containing silica extrudate was calcined in air at 350° C. for 3 hrs.

Example 4

1% Pt, 1.0% K on a Silica Support

A 1/20 inch (0.13 cm) quadrulobe silica extrudate was impregnated with 1.0 wt % K as potassium carbonate using incipient wetness impregnation and dried at 121° C. After drying the 1.0 wt % potassium containing silica extrudate was calcined in air at 538° C. The calcined 1.0% K containing silica extrudate was then impregnated with 1% Pt as tetraammine platinum hydroxide using incipient wetness impregnation and dried at 121° C. After drying the 1% Pt, 1.0% K containing silica extrudate was calcined in air at 350° C. for 3 hrs.

Example 5

1% Pt, 0% K on a Silica Support

A 1/20 inch (0.13 cm) quadrulobe silica extrudate was impregnated with 1% Pt as tetraammine platinum hydroxide using incipient wetness impregnation and dried at 121° C. After drying the 1% Pt, 0.0% K-containing silica extrudate was calcined in air at 350° C. for 3 hrs.

Example 6

Metal Dispersion

The catalysts in Examples 1 through 5 were evaluated for their metal dispersion using a Micromeritecs ASAP 2010 chemisorption apparatus. Hydrogen and oxygen dispersion values at a hydrogen reduction temperature of 250° C. are summarized in Table 1.

TABLE 1

| Catalyst  | Hydrogen Dispersion | Oxygen Dispersion |
|-----------|---------------------|-------------------|
| Example 1 | 103%                | 60%               |
| Example 2 | 119%                | 69%               |
| Example 3 | 124%                | 71%               |
| Example 4 | 182%                | 70%               |
| Example 5 | 98%                 | 50%               |

This table indicates that addition of K improves the Pt dispersion on the catalyst.

Example 7

Dehydrogenation of Cyclohexanone

The reactor used in these experiments consisted of a stainless steel tube with dimensions of 22 inches (56 cm) long×1/2 inch (1.3 cm) outside diameter×0.035 (0.09 cm) inch wall thickness. A piece of stainless steel tubing 8.75 inches (22 cm) long×0.375 inch (0.95 cm) outside diameter and a piece of 0.25 inch (0.64 cm) tubing of similar length was used in the bottom of the reactor as a spacer (one inside of the other) to position and support the catalyst in the isothermal zone of a furnace. A 0.25 inch (0.64 cm) plug of glass wool was placed at the top of the spacer to keep the catalyst in place. A 0.125 inch (0.32 cm) stainless steel thermo-well was placed in the catalyst bed, long enough to monitor temperature throughout the catalyst bed using a movable thermocouple.

The catalyst samples were pressed into pellets then crushed and sized to 20-40 US sieve mesh. Typically 5.0 grams, volume 12.5 cc. of the catalyst was pre sized to 20-40 mesh and used as a standard loading. The catalyst was then loaded into the reactor from the top. The catalyst bed typically was 15 cm in length. A 0.25 inch (0.64 cm) plug of glass wool was placed at the top of the catalyst bed to separate quartz chips from the catalyst. The remaining void space at the top of the reactor was filled with quartz chips. The reactor was installed in a furnace with the catalyst bed in the middle of the furnace at a pre marked isothermal zone. The reactor was then pressure and leak tested typically at 300 psig (2170 kPa, gauge).

Each catalyst was pre-conditioned in situ by heating to 375° C. to 460° C. with $H_2$ flow at 100 cc/min and holding for 2 hrs. A 500 cc ISCO syringe pump was then used to introduce a cyclohexanone feed to the reactor. The feed was pumped through a vaporizer before flowing through heated lines to the reactor. A Brooks mass flow controller was used to set the hydrogen flowrate. A Grove "Mity Mite" back pressure controller was used to control the reactor pressure typically at 100 psig (791 kPa, gauge). GC analyses were taken to verify feed composition. The feed was then pumped through the catalyst bed held at the reaction temperature of 375° C. to 460° C., preferably at 460° C. at a WHSV of 2-15 and a pressure of 100 psig (791 kPa, gauge). The products exiting the reactor flowed through heated lines routed to two collection pots in series, with the non-condensable gas products routed to an on line HP 5890 GC. The first pot was heated to 60° C. and the second pot cooled with chilled coolant to about 10° C. Material balances were taken 12 to 24 hrs intervals. Samples were taken and diluted with 50% ethanol for analysis. A Hewlett Packard 6890 gas chromatograph with FID detector and with an Agilent technologies GC column 30 m×0.32 mm×0.25 micron film thickness was used for the analyses of the hydrocarbon products. Non-condensable gas products analyses were taken on line via a HP 5980 Gas Chromatograph with J and W Scientific column 60 m×0.25 mm ID×1.0 micron film. The HP 6890GC analysis ramp program was set to: 40° C. for 0 min; 5° C./min to 150° C., held 0 min; 10° C./min to 260° C. held 28 min total analysis time was 60 min; and the HP 5890 GC ramp was set to: −30° C. for 5 min, 5° C./min to 80° C. for 2 min, 5° C./min to 200° C. for 0 min, 15° C./min to 240° C. held to the end total analysis time was 60 min.

FIG. 1 plots the production of light impurities (C4s, 2- or 3-methylpentane, hexane, 1-hexene, 1-pentene/pentane, and methylclopentane) and heavy impurities (diphenyl ether, 2-CH=1CHo1, 2 CH=1CHone, dibenzofuran, 2-phenylcyclohexanone, 4-pentylphenol, 2-phenylphenol, 2-cyclohexylphenol, 3-phenyl phenol, 4-phenylphenol and 2,6-diphenylphenol) against the potassium content of the catalysts tested. It will be seen that the total heavies and lights product concentration dropped below 1 wt % when the K content was between 0.15-0.6 wt % and below 0.5 wt % when the K content was between 0.2-0.5 wt %.

Figure 2:
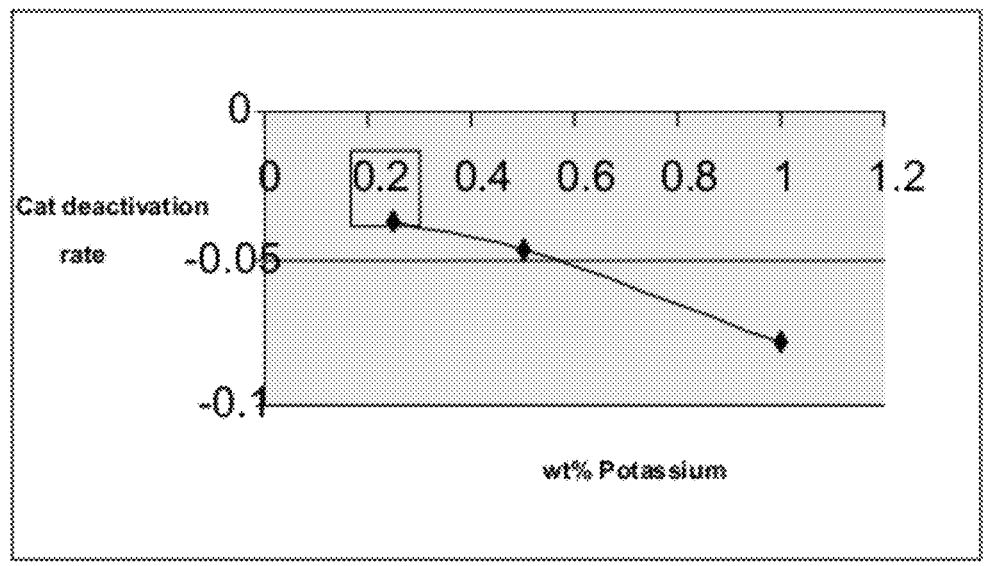
FIG. 2 is a graph of catalyst deactivation rate against the potassium (K) concentration of the catalyst in the process of dehydrogenating cyclohexanone described in Example 7.

FIG. 2 plots the catalyst deactivation rate as a function of the K loading of the catalyst and shows that the lowest catalyst deactivation rate was obtained at lower K content. Thus, although the data in Table 1 show that higher K content improves Pt dispersion, lower K values between 0.15-0.6 wt % improve catalyst stability and selectivity.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for the dehydrogenation of cyclohexanone to produce phenol, the process comprising contacting a feed comprising cyclohexanone under dehydrogenation conditions with catalyst composition comprising (i) a support; (ii) a dehydrogenation component comprising at least one metal or compound thereof selected from Groups 6 to 10 of the Periodic Table of Elements; and (iii) potassium or a potassium compound,
wherein the potassium is present in an amount of about 0.15 to about 0.6 wt % based upon the total weight of the catalyst composition,
wherein the catalyst composition is prepared by sequential impregnation with the potassium or potassium compound being applied to the support before the dehydrogenation component is applied to the support, and
wherein the catalyst composition has an oxygen chemisorption of greater than 50%.

2. The method of claim 1, wherein the potassium is present in an amount of about 0.2 to about 0.5 wt %, based upon the total weight of the catalyst composition.

3. The method of claim 1, wherein the support is selected from the group consisting of silica, a silicate, an aluminosilicate, zirconia, and carbon.

4. The method of claim 1, wherein the dehydrogenation component comprises at least one of platinum and palladium.

5. The method of claim 1, wherein the catalyst composition improves phenol selectivity relative to dehydrogenation catalysts containing greater than 0.6 wt % of potassium.

6. The method of claim 1, wherein the dehydrogenation component is present in an amount of about 0.01 to about 2 wt %, based upon the total weight of the catalyst composition.

7. The method of claim 1, wherein the dehydrogenation component is present in an amount of about 0.5 to about 1.5 wt % based upon the total weight of the catalyst composition.

8. A process for producing phenol from benzene, the process comprising:
(a) reacting benzene and hydrogen with a catalyst under hydroalkylation conditions to produce cyclohexylbenzene;
(b) oxidizing cyclohexylbenzene from (a) to produce cyclohexylbenzene hydroperoxide;
(c) converting cyclohexylbenzene hydroperoxide from (b) to produce an effluent stream comprising phenol and cyclohexanone; and
(d) contacting at least a portion of the effluent stream from (c) with a dehydrogenation catalyst comprising: (i) a support; (ii) a dehydrogenation component comprising at least one metal or compound thereof selected from Groups 6 to 10 of the Periodic Table of Elements; and (iii) potassium or a potassium compound, wherein the potassium is present in an amount of about 0.15 to about 0.6 wt % based upon the total weight of the catalyst composition, wherein the dehydrogenation catalyst is prepared by sequential impregnation with the potassium or potassium compound being applied to the support before the dehydrogenation component is applied to the support, and further wherein the contacting occurs under dehydrogenation conditions effective to convert at least part of the cyclohexanone in the effluent stream into phenol and hydrogen.

9. The process of claim 8, wherein the catalyst provides a reduced selectivity to one or more of pentane, pentene and carbon monoxide relative to dehydrogenation catalysts containing greater than 0.6 wt % of potassium.

* * * * *